US010814122B2

United States Patent
Hess, III et al.

(10) Patent No.: US 10,814,122 B2
(45) Date of Patent: Oct. 27, 2020

(54) FLOW CONTROL VALVE

(71) Applicant: AptarGroup, Inc., Crystal Lake, IL (US)

(72) Inventors: John Miller Hess, III, Midland, MI (US); Andrew Smith, Essexville, MI (US); Robert LaBean, Freeland, MI (US); Gregory Olechowski, Kawkawlin, MI (US); Mark Honard, Saginaw, MI (US)

(73) Assignee: AptarGroup, Inc., Crystal Lake, IL (US)

( * ) Notice: Subject to any disclaimer, the term of this patent is extended or adjusted under 35 U.S.C. 154(b) by 239 days.

(21) Appl. No.: 15/772,187

(22) PCT Filed: Oct. 30, 2015

(86) PCT No.: PCT/US2015/058299
§ 371 (c)(1),
(2) Date: Apr. 30, 2018

(87) PCT Pub. No.: WO2017/074420
PCT Pub. Date: May 4, 2017

(65) Prior Publication Data
US 2018/0311489 A1    Nov. 1, 2018

(51) Int. Cl.
*A61M 39/24* (2006.01)
*F16K 15/14* (2006.01)

(52) U.S. Cl.
CPC ..... *A61M 39/24* (2013.01); *A61M 2039/2426* (2013.01); *A61M 2039/2446* (2013.01); *F16K 15/14* (2013.01)

(58) Field of Classification Search
CPC .......... A61M 39/24; A61M 2039/2466; A61M 2039/064; A61M 2039/066;
(Continued)

(56) References Cited

U.S. PATENT DOCUMENTS 5,377,877 A    1/1995   Brown et al.
5,439,143 A    8/1995   Brown et al.
(Continued)

FOREIGN PATENT DOCUMENTS

| EP | 1 115 647 B1 | 1/2007 |
| WO | 2012134498 A1 | 10/2012 |
| WO | 2014089082 A1 | 6/2014 |

OTHER PUBLICATIONS

A prior art engineering drawing for a prototype valve assembly which was publicly displayed at a trade show.
(Continued)

*Primary Examiner* — Manuel A Mendez
*Assistant Examiner* — Justin L Zamory
(74) *Attorney, Agent, or Firm* — Wood, Phillips, Katz, Clark & Mortimer

(57) ABSTRACT

A flow control device (40) for controlling the flow of a pressurized fluent substance is disclosed. The device (40) includes a housing (44, 48, 52) having an inlet portion (44) for receiving the fluent substance, an outlet portion (48) for discharging the fluent substance, and a platform (52). The device (40) further has a valve (56) located within the housing (44, 48, 52). The valve (56) is located between the platform (52) and the outlet portion (48). The valve (56) has a flexible, resilient valve head portion (160) that has confronting, openable portions (212, 216) movable from a closed configuration to an open configuration when the valve head portion (160) is subjected to a pressure differential acting across the valve head portion (160).

12 Claims, 11 Drawing Sheets

(58) Field of Classification Search
CPC .. A61M 2039/0666; A61M 2039/0633; A61M 2039/0063; A61M 2039/0072; A61M 2039/2406; A61M 2039/242; A61M 2039/2426; A61M 2039/246; F16K 15/145

See application file for complete search history.

(56) References Cited

U.S. PATENT DOCUMENTS

| | | | |
|---|---|---|---|
| 5,839,614 A | 11/1998 | Brown | |
| 6,062,435 A | 5/2000 | Hess | |
| 6,065,642 A | 5/2000 | Brown | |
| 6,112,952 A | 9/2000 | Hess, III et al. | |
| 6,273,296 B1 | 8/2001 | Brown | |
| 6,279,783 B1 | 8/2001 | Brown et al. | |
| 6,427,874 B2 | 8/2002 | Brown et al. | |
| 6,749,092 B2 | 6/2004 | Olechowski et al. | |
| 7,077,296 B2 | 7/2006 | Brown et al. | |
| 7,086,572 B2 | 8/2006 | Socier et al. | |
| 7,784,652 B2 | 8/2010 | Gaus et al. | |
| 8,079,385 B2 | 12/2011 | Hatton | |
| 8,196,608 B2 | 6/2012 | Hatton | |
| 8,627,852 B2 | 1/2014 | Hatton | |
| 8,628,056 B2 | 1/2014 | LaBean et al. | |
| 8,814,849 B1* | 8/2014 | Winsor | A61M 39/24 604/537 |
| 2007/0080177 A1 | 4/2007 | Hatton et al. | |
| 2009/0188950 A1 | 7/2009 | Gaus et al. | |
| 2009/0264832 A1 | 10/2009 | Dikeman et al. | |
| 2010/0193516 A1* | 8/2010 | LaBean | B65D 47/2031 220/229 |
| 2010/0298782 A1 | 11/2010 | Winsor et al. | |
| 2011/0015580 A1 | 1/2011 | Stroup | |
| 2014/0224356 A1* | 8/2014 | Hatton | A61M 39/045 137/522 |

OTHER PUBLICATIONS

International Search Report and Written Opinion dated Jan. 22, 2016.

European Search Report, dated May 22, 2019 in the counterpart European Patent Application No. 15 907 513.4.

* cited by examiner

FLOW CONTROL VALVE

CROSS-REFERENCE TO RELATED APPLICATIONS

This application claims priority of Appln. No. PCT/US15/58299, filed Oct. 30, 2015, the disclosure of which is hereby incorporated by reference in its entirety.

TECHNICAL FIELD

The present invention relates generally to a flow control device, which can be advantageously used for patient care and like medical applications, and more particularly to a device for intravenous flow control.

BACKGROUND OF THE INVENTION AND TECHNICAL PROBLEMS POSED BY THE PRIOR ART

Many medical applications require flow-controlling devices for controlling flow of pressurized, fluent substances from a supply system for intravenous administration, enteral nutritional administration, and like patient care. To promote efficient use for various medical applications, systems and devices for administering solutions and other compounds can be configured to facilitate use for certain applications. For example, certain medical applications require a flow-controlling device having a valve to control certain flow characteristics, and further to prevent reverse-flow conditions.

The inventors of the present invention have discovered that, at least in some applications, administration of fluent substances through a flow control device having a valve may result in a degraded functionality of the valve, diminished reverse-flow prevention capabilities of the valve, valve misalignment, failure of the valve to fully close, fluent substance being dispensed with undesirable characteristics, and/or an inadequate discharge flow or quantity of the fluent substance or an over-dose discharge flow or quantity of the fluent substance. The inventors have further discovered that one or more of the above discussed undesirable flow control device conditions or undesirable characteristics may be more likely to occur during administration of fluent substances containing suspended particulate matter.

The inventors of the present invention have determined that for at least some applications in which some types of fluent substances are administered to a patient, it may be desirable to provide a flow control device that can eliminate, or at least reduce or minimize, the above-described undesirable flow control device conditions or flow characteristics.

The inventors of the present invention have also determined that it would be desirable to provide, at least for one or more types of applications, an improved flow control device that can be configured with a fluent substance supply system so as to have one or more of the following advantages: (1) ease of manufacture and/or assembly, and (ii) relatively low cost of manufacture and/or assembly.

BRIEF SUMMARY OF THE INVENTION

The inventors of the present invention have discovered how to provide an improved flow control device for controlling flow of a pressurized, fluent substance from a supply system that has an opening between the exterior and interior of the system. The flow control device can be used with a fluent substance dispensing system, and, especially in applications involving a fluent substance containing a suspended particulate, can prevent or minimize reverse flow conditions, degraded reverse-flow prevention of the valve, valve misalignment, failure of the valve to fully close, fluent substance being dispensed with undesirable characteristics, and/or an inadequate discharge flow or quantity of the fluent substance or an over-dose discharge flow or quantity of the fluent substance.

According to one aspect of the invention, the flow control device is provided to control the flow of a pressurized fluent substance. The flow control device has a housing with an inlet portion defining an inlet passage for accommodating flow of a pressurized fluent substance. The housing further has an outlet portion defining an outlet passage for accommodating flow of a pressurized fluent substance. The housing further has a platform.

The flow control device has a valve located between the inlet passage and the outlet passage. The valve has a flexible, resilient head portion with an inlet surface facing the inlet passage, and an outlet surface facing the outlet passage. The valve head portion further has at least one self-sealing slit through the head portion to define confronting, openable portions along the at least one self-sealing slit in an initially closed configuration. The openable portions are movable from the closed configuration to an open configuration when the head portion is subjected to an opening pressure differential acting across the head portion. The valve has a peripheral portion located laterally outward of the head portion for being retained by the housing. The valve further has an intermediate connecting portion extending between the head portion and the peripheral portion.

The platform is located between the valve inlet surface and the housing inlet passage. The platform is configured to be abutted by the valve inlet surface when the pressure at the valve outlet surface exceeds the pressure at the valve inlet surface by a predetermined amount.

The valve intermediate connecting portion contacts at least one of the platform and the housing inlet portion when the valve openable portions are in the initially closed configuration.

BRIEF DESCRIPTION OF THE DRAWINGS

In the accompanying drawings forming part of the specification, in which like numerals are employed to designate like parts throughout the same.

FIG. 8 shows the valve openable portions of the valve illustrated in the open configuration that would occur when the valve is subjected to a sufficient pressure differential acting across the valve;

DESCRIPTION OF THE PREFERRED EMBODIMENTS

While the flow control device of this invention is susceptible of embodiment in many different forms, this specification and the accompanying drawings disclose only some specific forms as examples of the invention. The invention is not intended to be limited to the embodiments so described, however.

For ease of description, the flow control device of this invention is described, with reference to the drawings, in a generally vertical orientation in cooperation with a fluent substance supply system, wherein the fluent substance would enter the flow control device from below and exit the flow control device from above. The terms "axial" and "radial" are used herein with respect to an axis A (FIGS. 6, 7, 8, and 13), generally defined by the housing. As employed herein, the phrase "axially inwardly" refers to the direction toward the fluent substance supply system, or downwardly in the figures. The phrase "axially outwardly" refers to the direction away from the fluent substance supply system, or upwardly in the figures. It will be understood, however, that this invention may be manufactured, stored, transported, used, and sold in orientations other than the orientation shown.

The flow control device of this invention is suitable for use with a variety of conventional or special pressurized fluent substance supply systems having various designs, the details of which, although not illustrated or described, would be apparent to those having skill in the art and an understanding of such systems.

Figures illustrating the components of the inventive flow control device in cooperation with a fluent substance supply system show some conventional mechanical or structural features that are known to, and that will be recognized by, one skilled in the art. The detailed descriptions of such features are not necessary to an understanding of the invention, and accordingly, are herein presented only to the degree necessary to facilitate an understanding of the novel aspects of the present invention.

Figure 1:
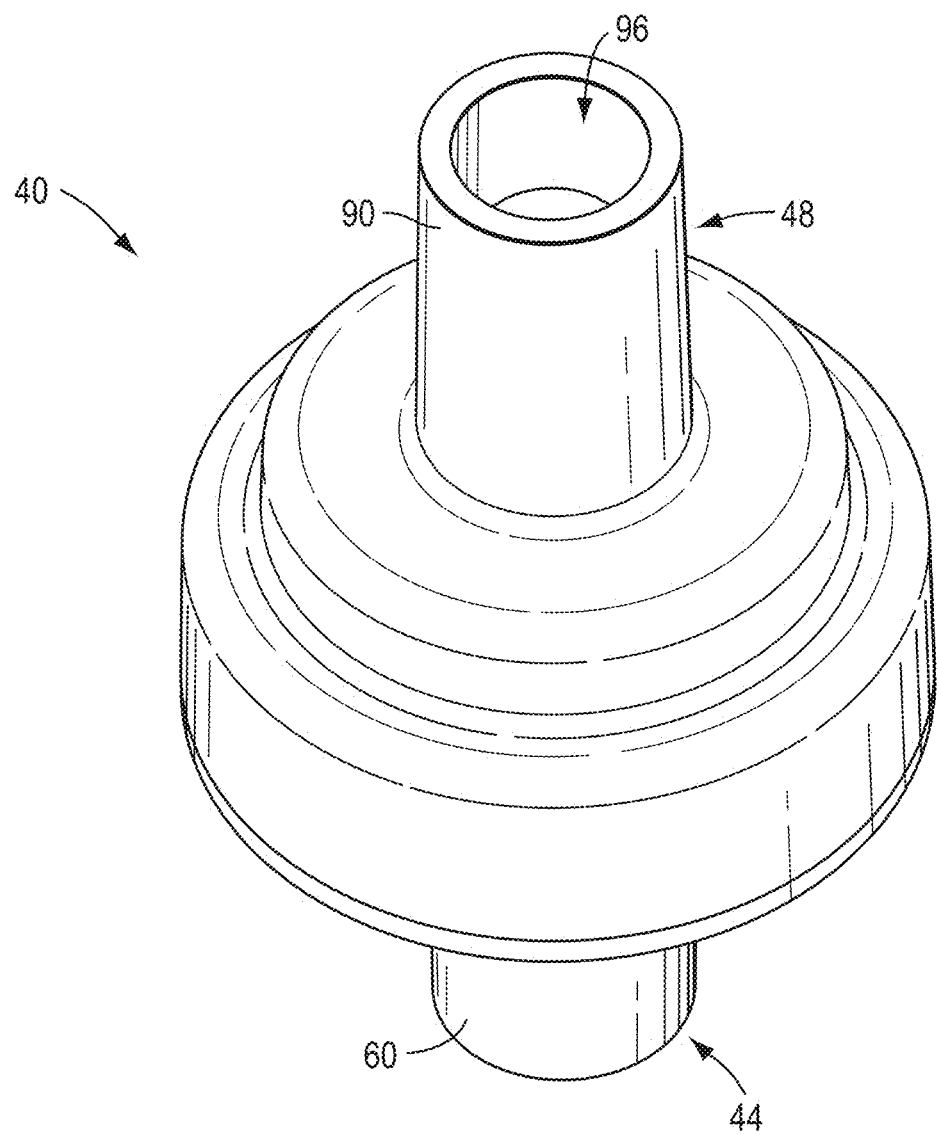
FIG. 1 is a perspective view, taken from above, of a first embodiment of a flow control device of the present invention for controlling the flow of a pressurized fluent substance from a supply system (not shown in FIG. 1)

FIG. 1 illustrates a first embodiment of a flow control device 40 as used for controlling the flow of a pressurized, fluent substance from a supply system (not illustrated). The flow control device 40 is adapted to be in communication with the interior of the supply system, and in the particular embodiment illustrated in FIG. 1, the flow control device 40 is especially adapted to be installed in an intravenous flow path in communication with the supply system, or otherwise associated with the supply system, in a manner that permits the communication between the flow control device 40 and the interior of the supply system. In another embodiment (not illustrated), some portion or portions of the flow control device 40 could be formed as an integral structure that is a unitary part of the supply system.

The supply system may be, for example, an intravenous fluent bag or container, tank, reservoir, fluent substance processing system, or fluent substance delivery system, which contains a pressurized fluent substance (including a system in which the pressure results from the static head of the fluent substance within the system and/or in which the system generates or otherwise creates a pressurized fluent substance therein).

Figure 2:
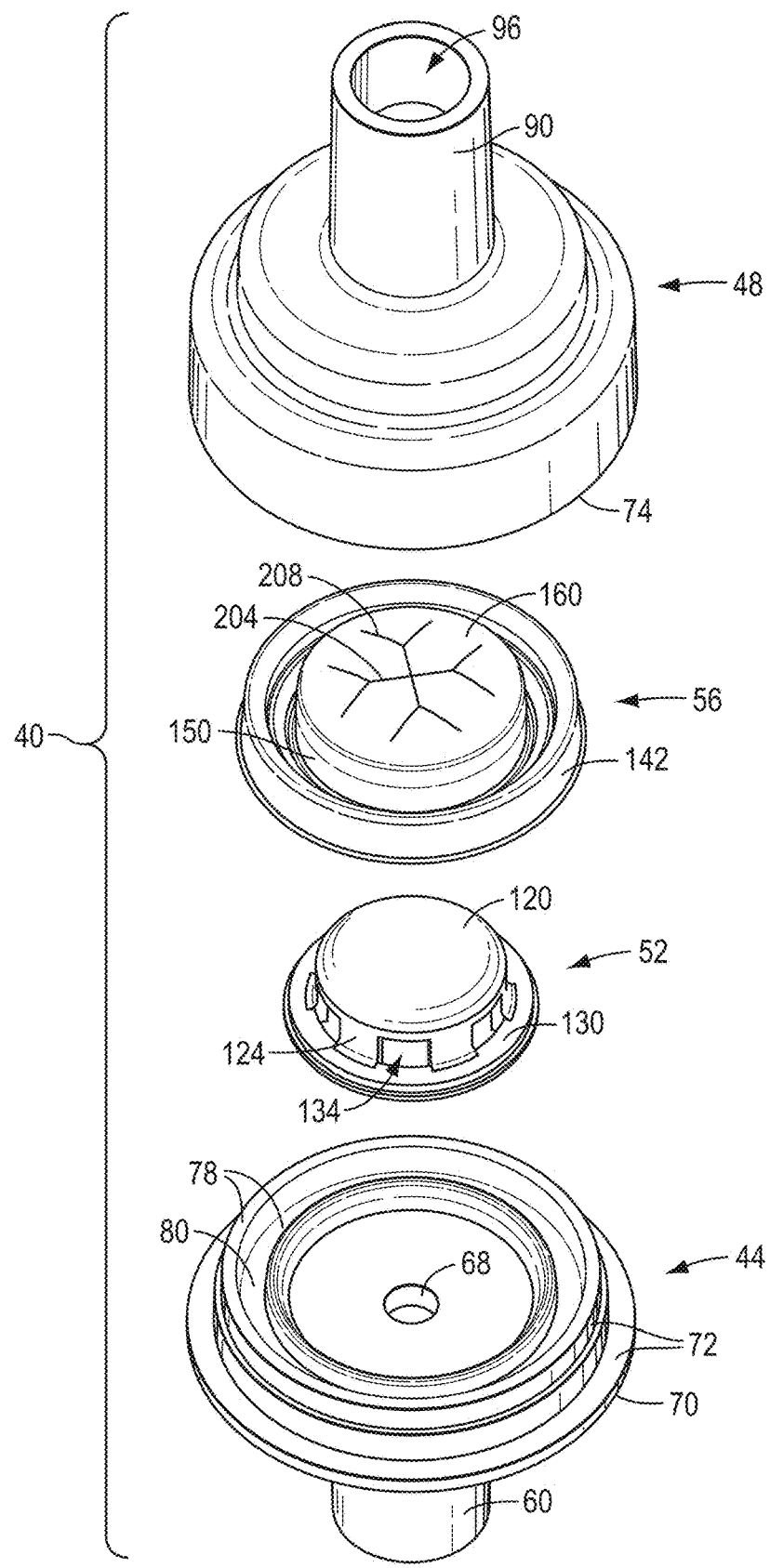
FIG. 2 an exploded, perspective view of the first embodiment of the flow control device illustrated in FIG. 1.
Figure 3:
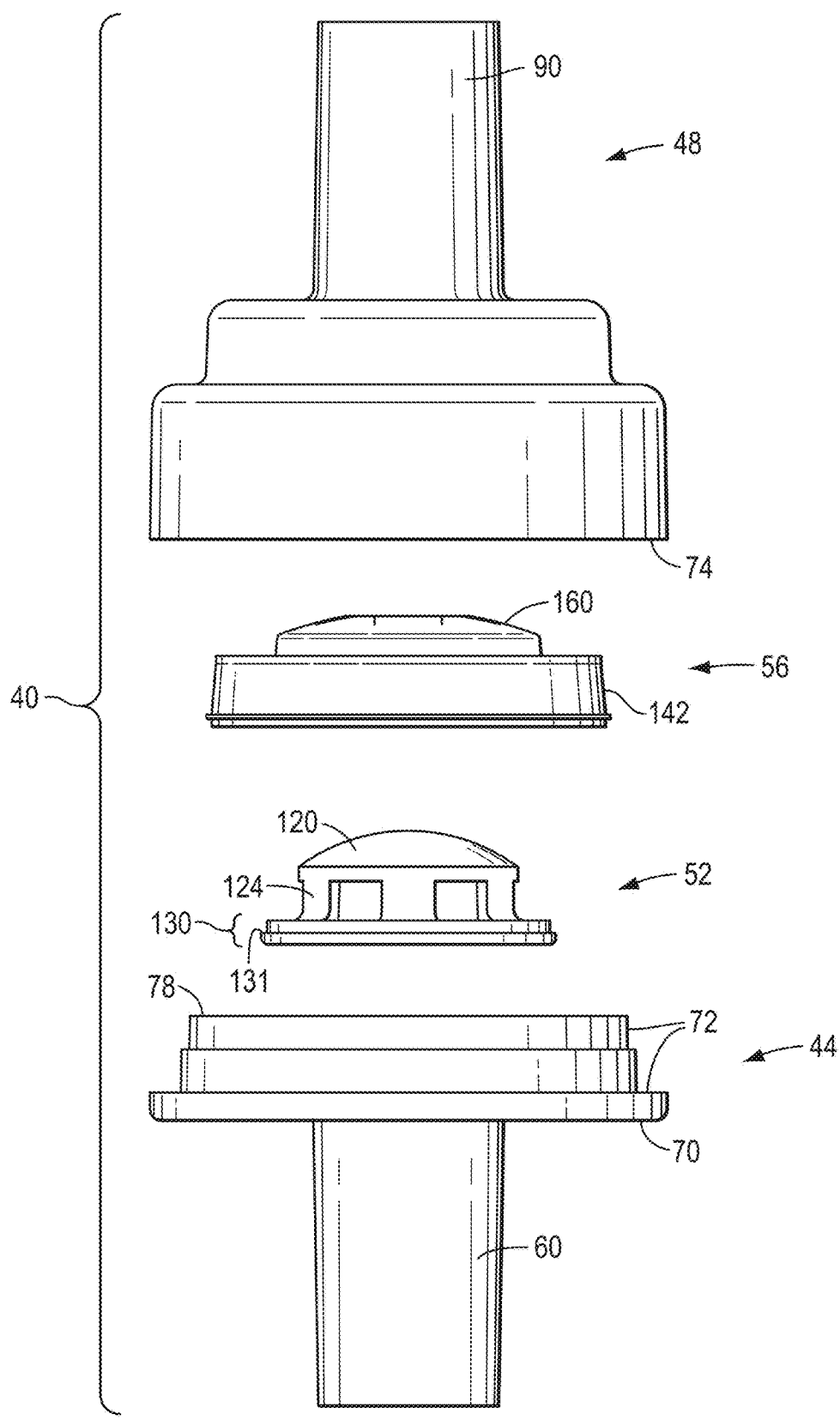
FIG. 3 an exploded, side elevation view of the first embodiment of the flow control device illustrated in FIG. 1.
Figure 4:
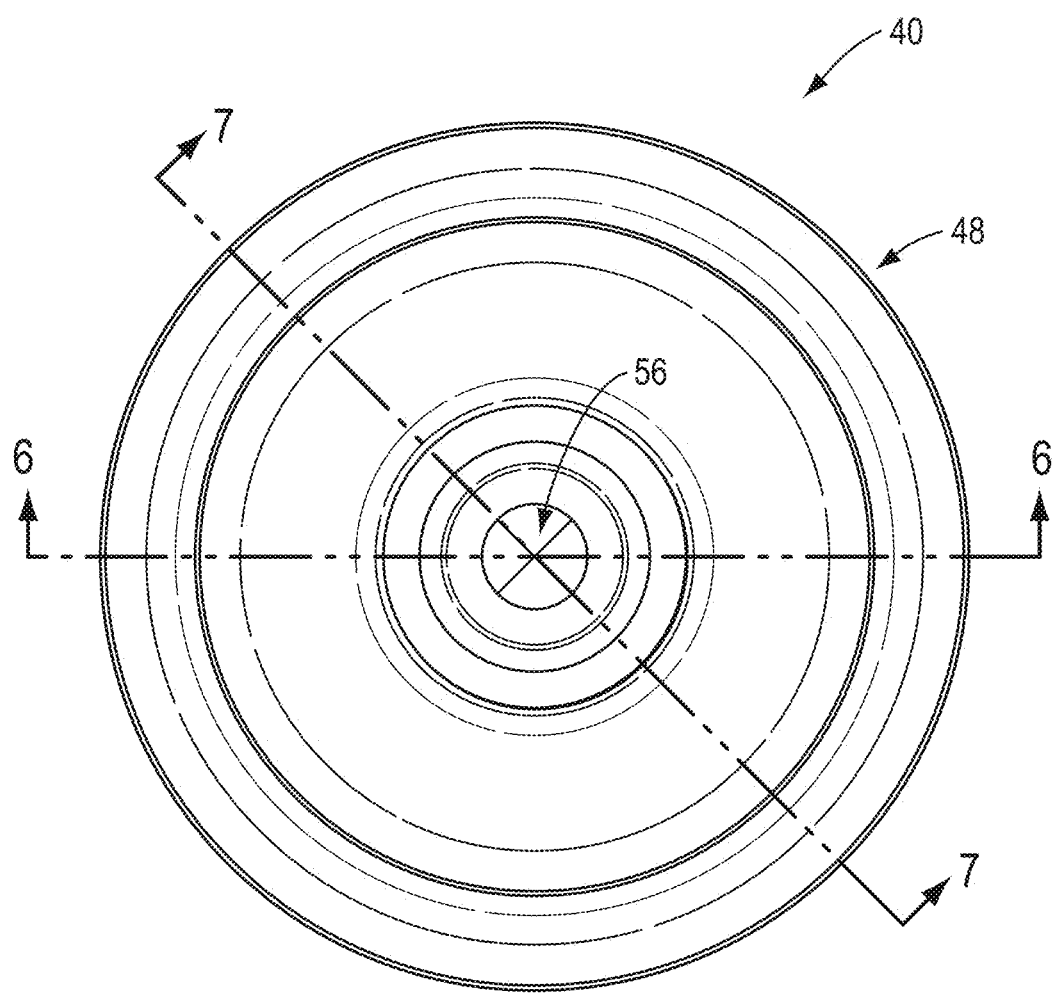
FIG. 4 is a top plan view of the first embodiment of the flow control device illustrated in FIG. 1.
Figure 5:
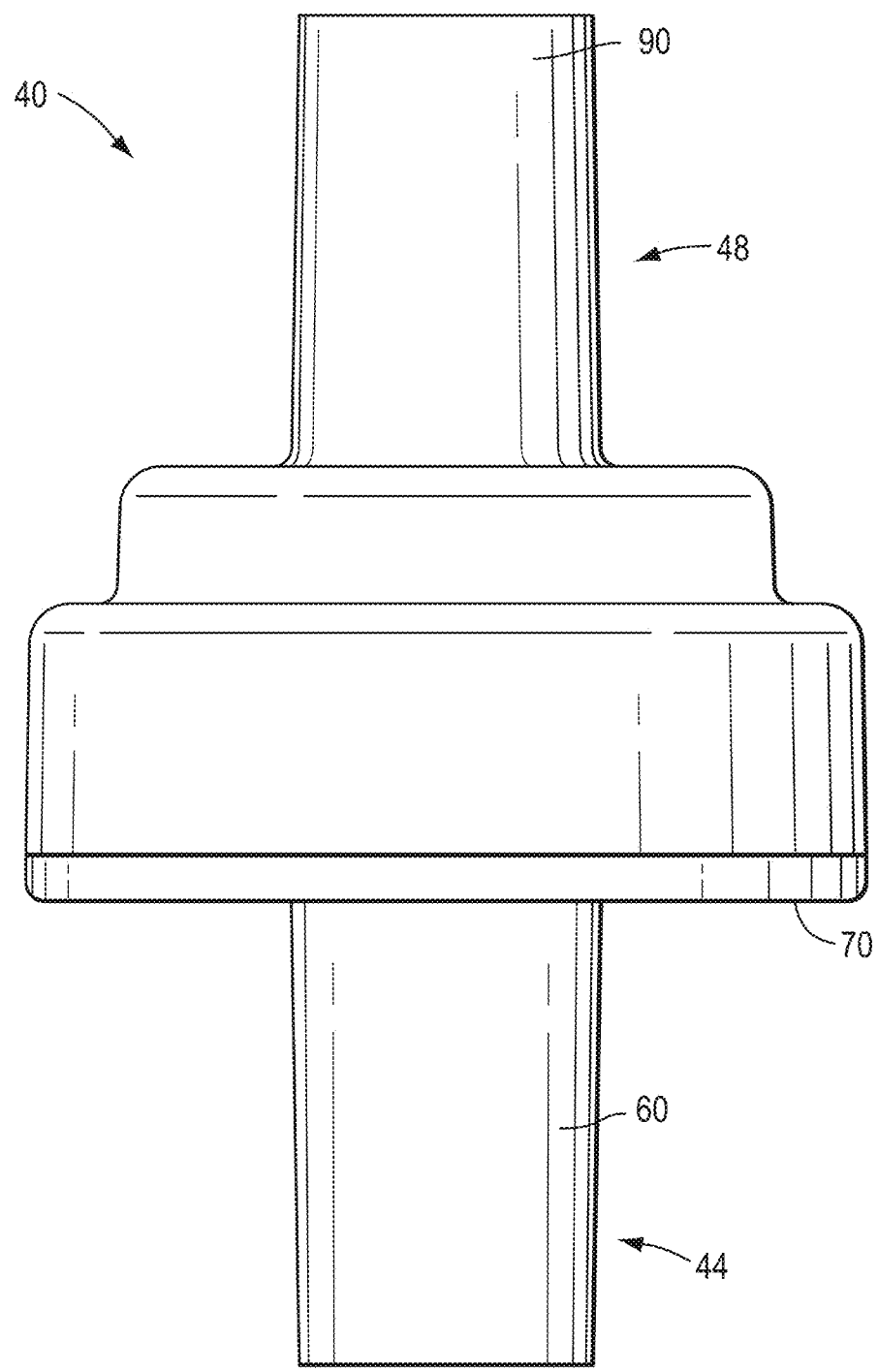
FIG. 5 is a side elevation view of the first embodiment of the flow control device illustrated in FIG. 1.

With reference to FIGS. 2 and 3, the first presently preferred embodiment of the flow control device 40 includes four components: a housing inlet portion 44; a housing outlet portion 48; a housing button or platform 52; and a valve 56.

Figure 6:
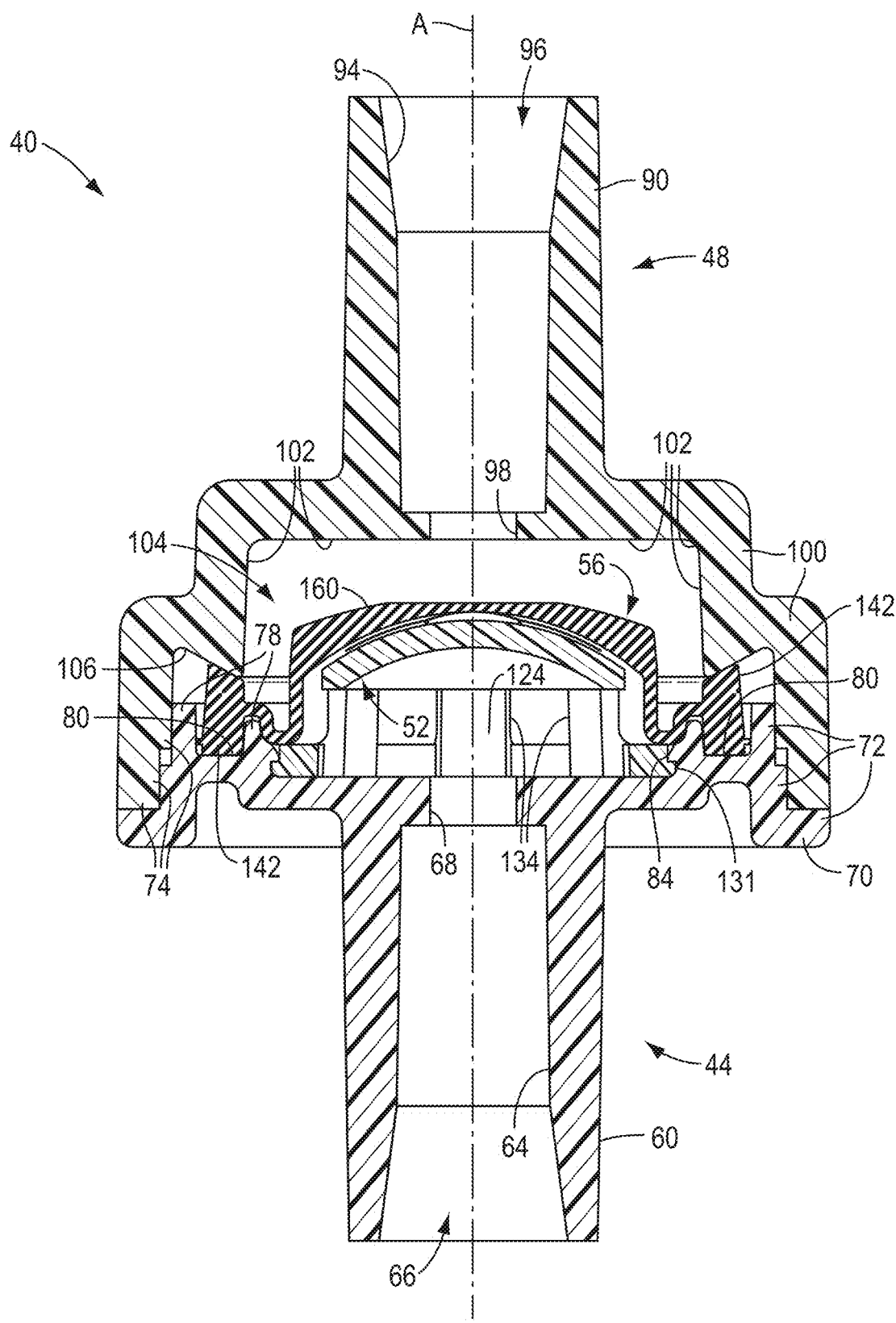
FIG. 6 is a cross-sectional view of the first embodiment of the flow control device taken generally along the plane 6-6 in FIG. 4.
Figure 7:
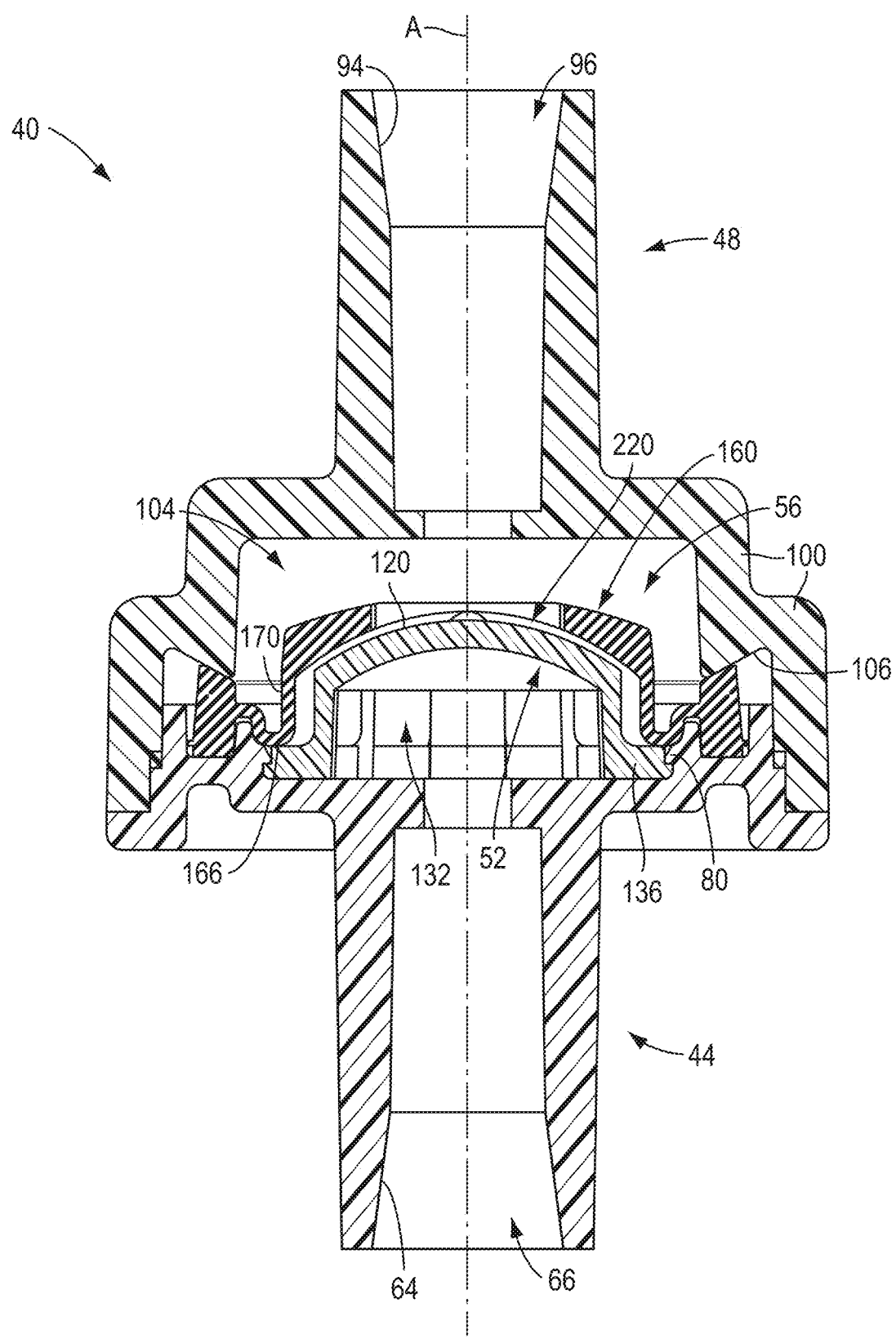
FIG. 7 is a cross-sectional view of the first embodiment of the flow control device taken generally along the plane 7-7 in FIG. 4.
Figure 8:
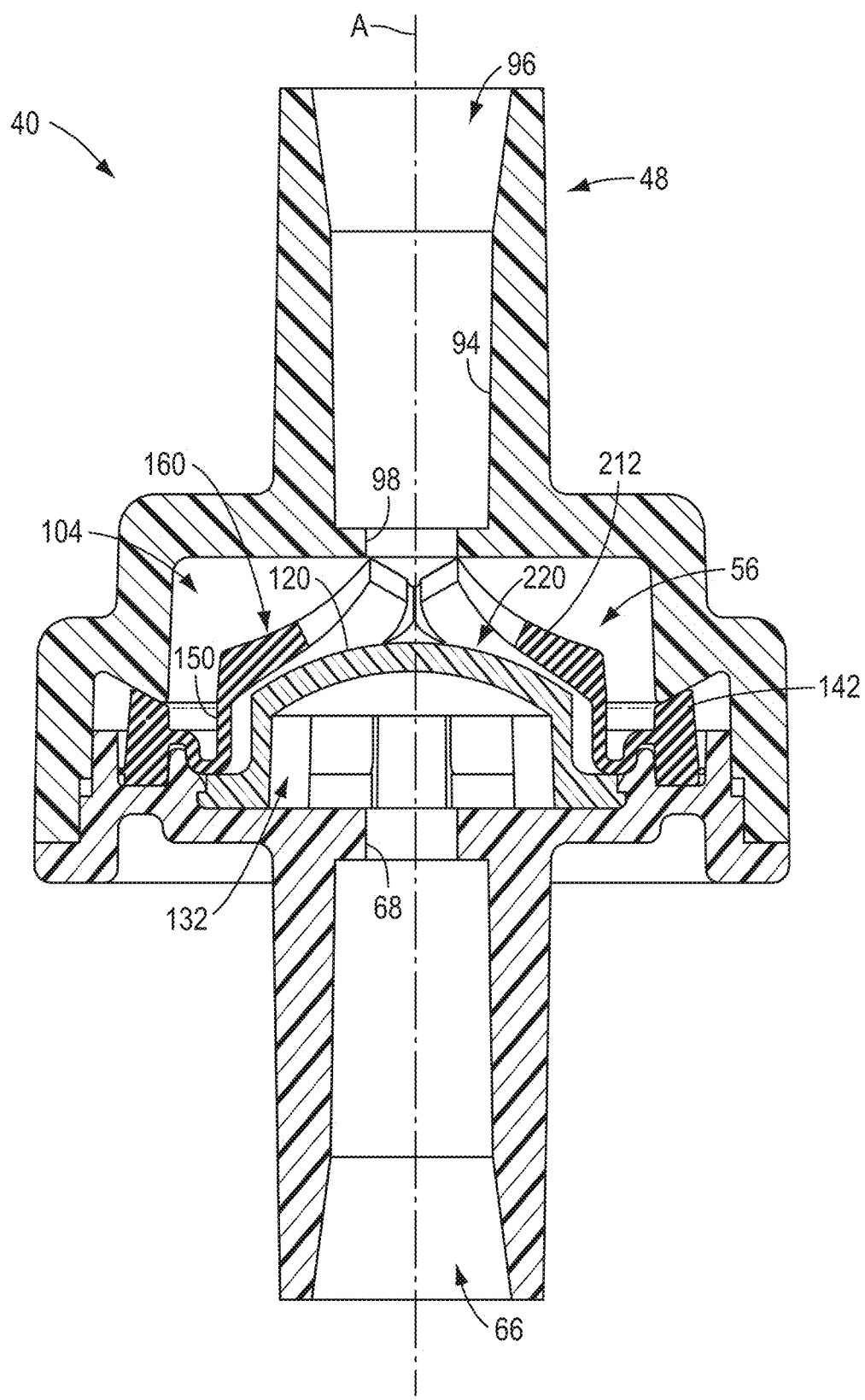
FIG. 8 is a view similar to FIG. 7, except

As shown in FIGS. 6-8, the platform 52 is preferably configured to be attached to the housing inlet portion 44. The housing inlet portion 44 and the housing outlet portion 48 are configured to be attached together to clamp the valve 56 between them, with the valve 56 located between the housing outlet portion 48 and the platform 52. Together, the housing inlet portion 44, the housing outlet portion 48, and the platform 52 may be characterized as defining a "housing" 44, 48, 52 that can be fluidly connected to the opening of a supply system (not illustrated) containing a fluent substance (not illustrated). More particularly, the housing inlet portion 44 may be connected via tubing (not illustrated) to the opening of the supply system for receiving a fluent substance, and the housing outlet portion 48 may be fluidly connected to a patient's vein via tubing extending from the housing outlet portion 48 and terminating in the patient's vein via a needle attached to the tubing.

With reference to FIG. 6, the housing inlet portion 44 may be characterized as having a generally annular wall 60 that may be received in, or may receive, a fluid connection (e.g., connector tubing) from the supply system (not illustrated) and that may be connected thereto (e.g., such as by an internal glue joint). The wall 60 has an interior surface 64 that defines an inlet passage 66 and a recessed, reduced diameter inlet orifice 68 for receiving the fluent substance. The inlet orifice 68 allows communication of the fluent substance from the supply system to the interior of the housing 44, 48, 52, as will be discussed in greater detail hereinafter.

As can be seen in FIGS. 2 and 6, the housing inlet portion 44 further has an annular flange 70 extending radially outwardly from the wall 60 and having a plurality of mating surfaces 72 for contacting a plurality of surfaces 74 of the housing outlet portion 48. The housing inlet portion mating surfaces 72 and the surfaces 74 of the housing outlet portion are configured to be engaged or otherwise attached to create a fluid-tight seal such as through ultrasonic welding, adhesive, interference fit, ENFit (enteral feeding connector), luer lock, threaded luer lock, or screw threaded connection (not illustrated).

Still referring to FIGS. 2 and 6, the housing inlet portion 44 further has two internal, annular ribs 78 defining a channel or valve seating surface 80 for receiving a portion of the valve 56 (FIG. 6), as described in detail hereinafter.

The radially-innermost, internal, annular rib 78 has a snap-fit retaining bead 84 for retaining the platform 52 in the housing inlet portion 44. It will be appreciated that the housing inlet portion 44 may have a plurality of retaining beads 84 for retaining the platform 52 (such an alternative not being illustrated). Alternatively, the housing inlet portion 44 need not have any retaining bead 84, and may instead retain the platform 52 by ultrasonic welding, adhesive, interference fit, EnFit, luer lock, threaded luer lock, or screw threaded connection to the housing inlet portion 44 (not illustrated). The platform 52 need not be retained exclusively by the inlet portion 44, and instead may be alternatively loosely held within, or clamped by, the housing inlet and outlet portions 44 and 48 co-acting together.

Still referring to FIG. 6, the housing outlet portion 48 may be characterized as having a generally annular wall 90 that may be received in, or may receive a fluid connection (e.g., connector tubing) extending from a patient (not illustrated) and that may be connected thereto (e.g., such as by an internal glue joint). The wall 90 has an interior surface 94 that defines an outlet passage 96 and a reduced diameter outlet orifice 98 for accommodating the flow of the fluent substance. The outlet orifice 98 allows fluid communication of the fluent substance from the interior of the housing 44, 48, 52 to the patient, as will be discussed in greater detail hereinafter.

The housing outlet portion 48 further has a stepped, annular wall 100 that extends axially inwardly and radially outwardly from the wall 90 to define an annular shoulder. The stepped annular wall 100 has an internal surface 102 which defines an outlet chamber 104, the function of which will also be discussed in detail hereinafter. The stepped annular wall 100 further defines the aforementioned plurality of mating surfaces 74 for engaging the mating surfaces 72 of the housing inlet portion 44. It will be appreciated that the volume of the chamber 104 could be reduced to reduce the priming volume, or volume of air that would need to be primed or removed from the flow control device 40 during operation, which will also be discussed in detail hereinafter.

Referring now to FIG. 7, the housing outlet portion 48 further has a generally frustoconical surface or valve seating surface 106 for engaging a portion of the valve 56, the function of which will be discussed in detail hereinafter. It will be appreciated that valve seating surface 106 may have a variety of shapes, for engaging a portion of the valve 56 to retain the valve 56 within the housing 44, 48, 52, and need not be frustoconical (not illustrated).

Figure 9:
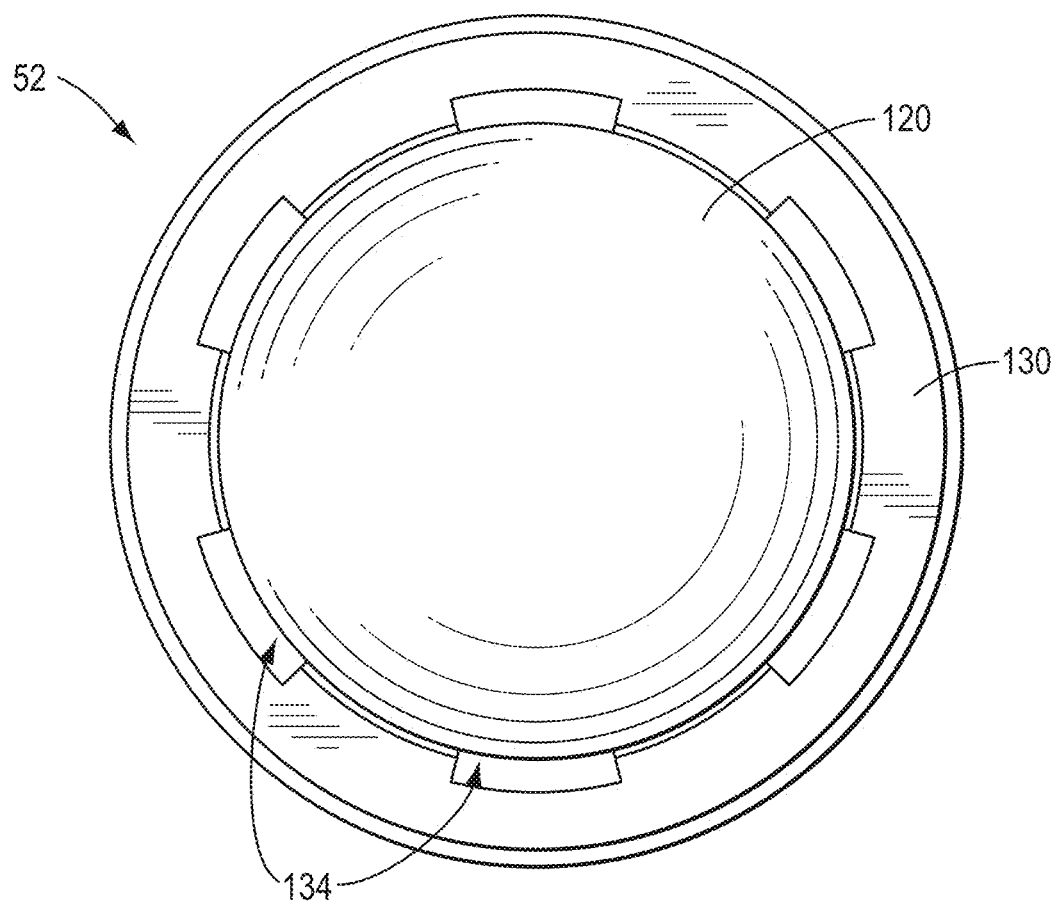
FIG. 9 is a top plan view of only the platform of the first embodiment of the flow control device shown in FIG. 2.
Figure 10:
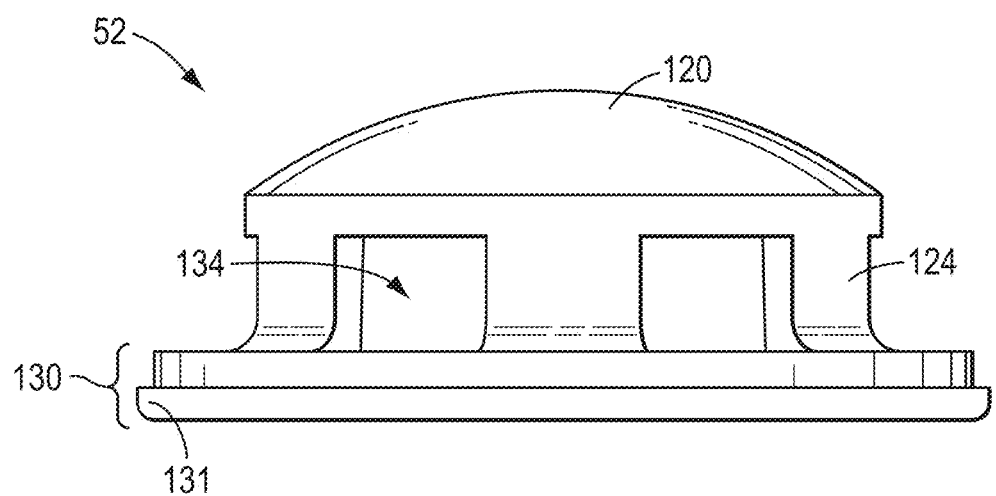
FIG. 10 is a side elevation view of the platform shown in FIG. 9.

With reference to FIGS. 7, 9, and 10, the platform 52 defines a dome-like, convex valve-confronting surface 120 for confronting a portion of the valve 56 (visible in FIG. 7 but not illustrated in FIGS. 9 and 10), the function of which will be discussed in detail hereinafter. The platform 52 further defines a plurality of spaced legs 124 (FIG. 10) that extend axially away from the valve-confronting surface 120 and which terminate in an annular skirt 130. The annular skirt 130 is preferably provided with an annular flange 131 (FIGS. 6 and 10). The legs 124 define an internal, platform chamber 132 (FIG. 7) having a plurality of windows or apertures 134 extending between the legs 124, allowing communication of the fluent substance between the platform chamber 132 (FIG. 7) and the valve-confronting surface 120. As can be seen in FIGS. 6 and 10, the annular flange 131 is provided for snap-fit engagement with the aforementioned retaining bead 84 of the housing inlet portion 44, thus securing the platform 52 within the housing inlet portion 44. While the housing inlet portion 44 and the platform 52 are preferably separately molded parts, it will be appreciated that the housing inlet portion and the platform could be unitarily molded (not illustrated).

Figure 11:
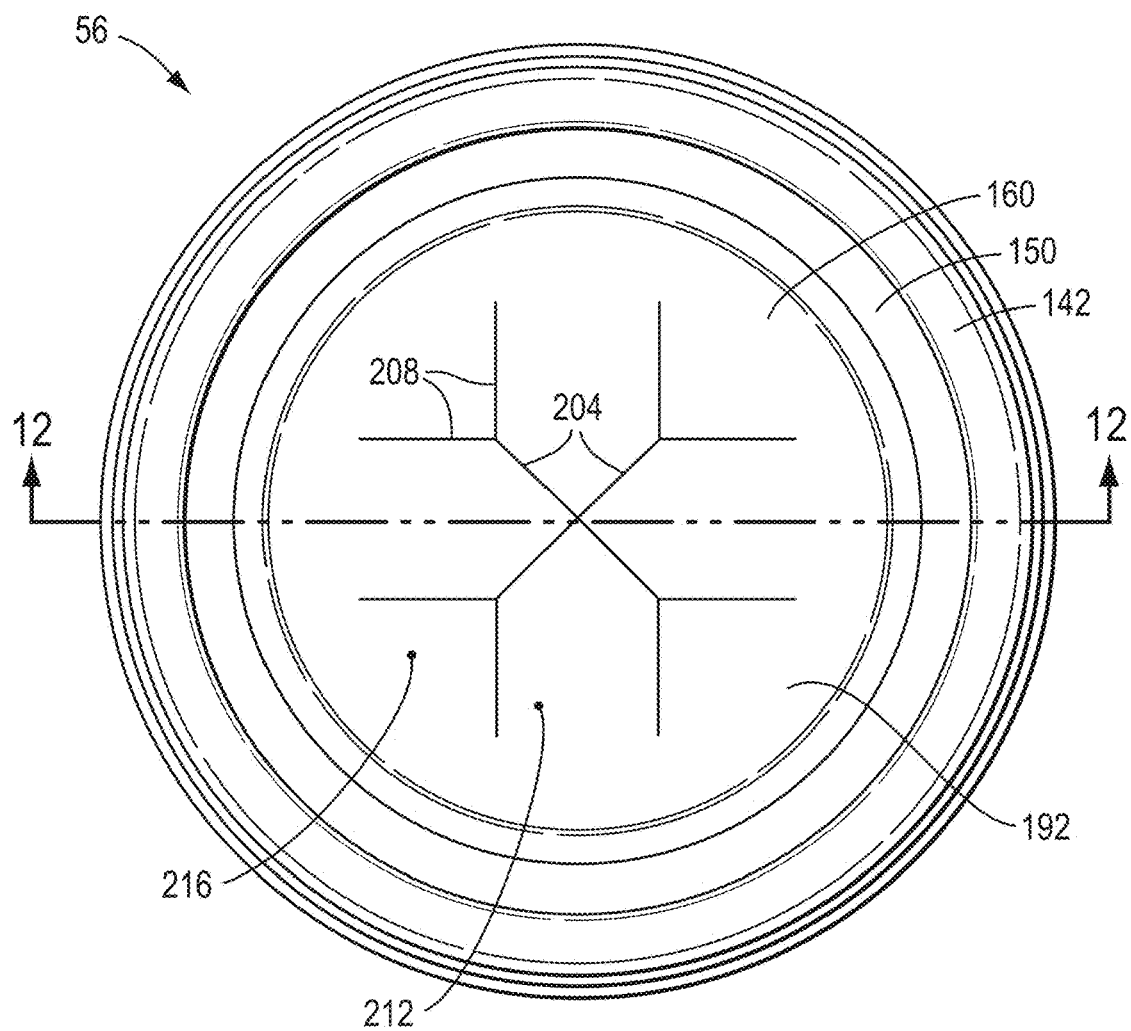
FIG. 11 is a top plan view of only the valve of the first embodiment of the flow control device shown in FIG. 1, the valve being located in the interior of the device and not visible in FIG. 1.
Figure 12:
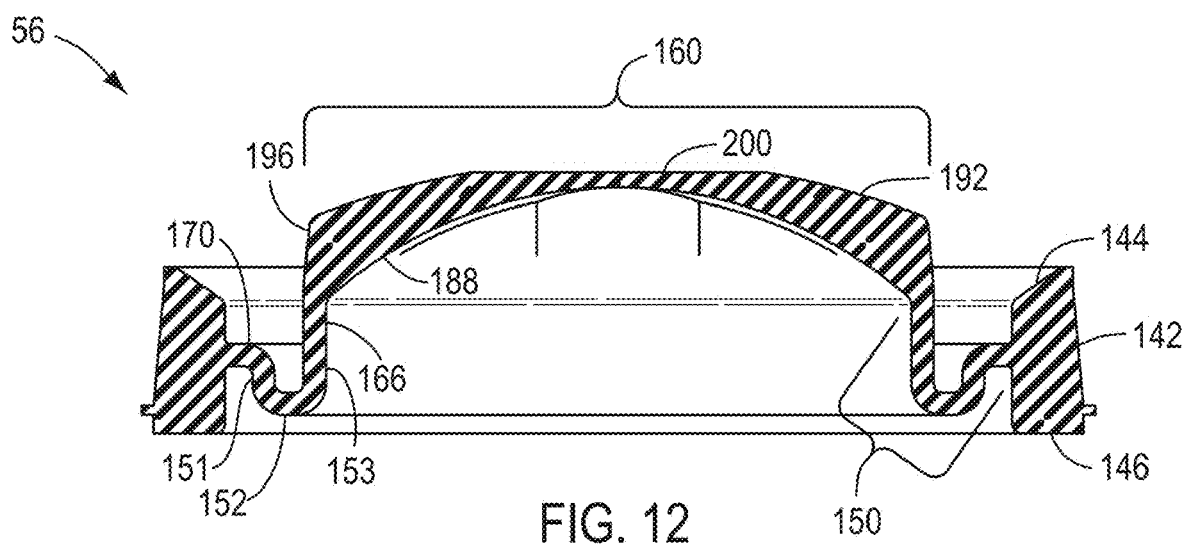
FIG. 12 is a cross-sectional view of the valve taken generally along the plane 12-12 in FIG. 11.

In the first illustrated embodiment of the flow control device 40, the valve 56 is a flexible, resilient, pressure-openable, self-closing, slit-type valve (as best shown in FIGS. 2, 11, and 12. Similar type valves are generally disclosed in the U.S. Pat. Nos. 5,839,614; 6,293,437; and 8,678,249. The descriptions of those patents are incorporated herein by reference thereto to the extent pertinent and to the extent not inconsistent herewith.

The valve 56 is suitable for use with fluent substances, such as liquids and gases, including, inter alia, intravenous fluids, liquids, mixtures, solutions, suspensions, and medicaments. The valve 56 is preferably molded as a unitary structure (i.e., one-piece structure) from material which is flexible, pliable, elastic, and resilient. This can include elastomers, such as a synthetic, thermosetting polymer, including silicone rubber, such as the silicone rubber sold by Dow Corning Corporation in the United States if America under the trade designation D.C. 99-595 and RBL-9595-40. Another suitable silicone rubber material is sold in the United States of America under the designation Wacker 3003-40 by Wacker Silicone Company. The valve 56 could also be molded from other thermosetting materials or from other elastomeric materials, or from thermoplastic polymers or thermoplastic elastomers, including those based upon materials such as thermoplastic propylene, ethylene, urethane, and styrene, including their halogenated counterparts. For example, a particular non-silicone material that may be employed is ethylene propylene diene monomer rubber ("EPDM"), such as sold in the United States of America under the designation Grade Z1118 by Gold Key Processing, Inc. having an office at 14910 Madison Road, Middlefield, Ohio 44062, United States of America. Another non-silicone material that may be employed is nitrile rubber, such as sold in the United States of America under the designation Grade GK0445081-2 by Graphic Arts Rubber, having an office at 101 Ascot Parkway, Cuyahoga Falls, Ohio 44223, United States of America. It is desirable in many applications that the material be substantially inert so as to avoid reaction with, and/or adulteration of, the fluent substance in contact with the valve.

The valve 56 has an initially closed, unactuated, substantially unstressed, rest position or configuration (as best seen in FIGS. 11 and 12). The valve 56 can be forced to an "open" position or configuration (FIG. 8) when a sufficiently high pressure differential acts across the valve 56 as described hereinafter.

With reference to FIG. 12, the valve 56 has a peripheral mounting portion or flange 142. The flange 142 may have any suitable configuration for being mounted to, attached to, connected with, or for otherwise being retained between the housing inlet portion 44 (not illustrated in FIG. 12) and the housing outlet portion 48 (not illustrated in FIG. 12) in which the valve 56 is installed. Preferably, the mounting flange 142 is somewhat resiliently compressed so as to accommodate the creation of a secure, leak-resistant seal, under relatively high and low pressures, when the valve flange 142 is compressively engaged between the housing inlet portion 44 and the housing outlet portion 48. To that end, as seen in FIGS. 6 and 7, the valve flange 142 includes a frustoconical surface 144 for engaging the mating frustoconical, valve seating surface 106 on the housing outlet portion 44, and the valve flange 142 also includes a substantially flat surface 146 for engaging the mating flat valve seating surface 80 on the housing inlet portion 44 (visible in FIGS. 2 and 6, but not illustrated in FIG. 12).

With appropriate modification of the housing inlet portion 44 and the housing outlet portion 48, other shapes could be used for the valve flange 142. Some other shapes of flange cross sections which could be employed on the valve 56 are illustrated in the U.S. Pat. No. 5,409,144. In some applications, it may be desirable to configure the flange 142 for attachment to one or both of the housing portions 44, 48, 52 by means of adhesive, bi-injection molding, heat bonding, or other suitable means.

Extending laterally or radially inwardly from the valve flange 142 is a generally annular, intermediate connecting portion or sleeve 150 which connects the flange 142 to a valve head portion 160. The intermediate connecting portion 150 may be characterized as having an inlet side 166 (FIG. 12) generally confronting the platform 52 and the housing inlet portion 44 (FIG. 7) when the valve 56 is installed in the housing 44, 48, 52 (FIG. 7). The intermediate connecting portion 150 may be further characterized as having an outlet side 170 generally exposed to the housing outlet portion 48 (FIG. 7) when the valve 56 is installed in the housing 44, 48, 52. As can be seen in FIGS. 6-8, at least a portion or part of the intermediate connecting portion 150 contacts a portion of the housing to further enhance the rigidity of the valve 56 and prevent opening of the valve 56 under reverse flow conditions. The intermediate connecting portion 150 preferably has a generally U-shaped cross-sectional configuration (as viewed along a plane, containing the longitudinal axis A of the flow control device 40). More particularly, with reference to FIG. 12, the U-shaped configuration of the intermediate portion 150 extends axially in a first leg 151, laterally in a second leg 152, and axially in a third leg 153 that is generally parallel to the first leg 151. The generally U-shaped cross-sectional configuration of the intermediate connecting portion 150 functions to, among other things, assist in stabilizing and aligning the valve 56 within the housing 44, 48, 52 prior to and during assembly and operation.

The valve head portion 160 is flexible and resilient. As can be seen in FIGS. 11 and 12, the valve head portion 160 has a generally circular configuration relative to longitudinal axis A defined by the housing 44, 48, 52 (see FIGS. 7 and 8). With reference to FIG. 12, the valve head portion 160 may be characterized as having an inlet surface or side 188 facing in the axially inward direction, and may be further characterized as having an outlet surface or side 192 facing in the axially outward direction. When the valve 56 is closed, the head portion 160 has a concave configuration when viewed from the inlet side 188, and the head portion 160 has a generally convex configuration when viewed from the outlet side 192.

The valve 56 is flexible and changes configuration between (1) a retracted, closed, rest position (as shown in FIGS. 6 and 7), and (2) an extended, active, open position (as shown in FIG. 8). The fluent substance can be dispensed (i.e., discharged) through the valve 56 in a discharge flow direction along the longitudinal axis A when the valve 56 opens as shown in FIG. 8.

With reference to FIG. 12, the outer perimeter of the valve head 160 is preferably defined by a slightly tapered, peripheral, marginal surface 196 which begins at an axially outwardly peripheral corner of the valve head 160 and extends axially inwardly therefrom with a slight taper to ultimately terminate at the thinner, intermediate portion 150. The valve head 160 further has a central portion 200 that has a planar, circular configuration when the valve head 160 is in the fully retracted, closed, position.

When the valve head portion 160 is viewed in cross section as illustrated in FIG. 12, the valve head portion 160 is somewhat thicker at a radially outside region of the valve head portion 160, and is thinner at a radially inside region of the valve head portion 160. This configuration assists in providing a desirable opening action and closing action. In some applications (not illustrated), the valve head portion, intermediate connecting portion, and/or the flange portion could have a uniform thickness.

With reference to FIG. 11, the valve head portion 160 has a normally closed orifice defined by a plurality of primary slits 204 radiating laterally or radially from the center of the valve head portion 160. The valve head portion 160 further has a plurality of secondary slits 208 branching from the radially outward ends of the primary slits 204. The illustrated embodiment of the valve 56 has four intersecting primary slits 204, and eight secondary slits 208 branching therefrom. A lesser or greater number of primary slits 204 and secondary slits 208 could be used depending on the flow characteristics required by the application of the flow control device 40. The slits 204, 208 extend transversely through the valve head portion 160 from the inlet side 188 to the outlet side 192. In the illustrated embodiment of the valve 56, the slits 204 and 208 are of equal length, respectively, although the slits could be of unequal lengths (not illustrated).

The primary slits 204 define four, generally pentagonal-shaped, equally sized flaps or primary petals 212 (FIGS. 8 and 11) in the valve head portion 160. As can be seen in FIG. 11, the secondary slits 208 define four, generally triangular-shaped, equally sized flaps or secondary petals 216 in the valve head portion 160. The primary and secondary petals 212, 216 may be also characterized as "openable regions" or "openable portions" of the valve head portion 160. Each primary petal 212 has a plurality of transverse faces defined by the primary slits 204, and each transverse face seals against a confronting transverse face of an adjacent primary petal 212 when the valve 56 is closed. Likewise, each secondary petal 216 has a pair of diverging transverse faces defined by the secondary slits 208, and each transverse face seals against a confronting transverse face of an adjacent secondary petal 216 when the valve 56 is closed. Forms of such a type of slits in a valve are disclosed in the U.S. Pat. No. 8,628,056. The description of that patent is incorporated herein by reference thereto to the extent pertinent and to the extent not inconsistent herewith.

The valve 56 can be molded with the slits 204/208. Alternatively, the valve slits 204/208 can be subsequently stamped or cut into the valve head portion 160 by suitable conventional techniques. In operation, the petals 212, 216 can be forced open outwardly (FIG. 8) from the intersection points of the slits 204 and 208 when a sufficient force is applied to the inlet side 188 to a pressure that head portion 160 (e.g., as by subjecting the valve inlet side 188 to a pressure that is greater than the pressure on the outlet side 192 to establish a pressure differential across the valve head portion 160 that is sufficiently large to overcome the resilient closing force of the valve head portion 160).

The valve head portion 160, intermediate portion 150, and slits 204, 208 are preferably configured for use in conjunction with a particular system, and a specific type of fluent substance, so as to achieve the flow characteristics desired. For example, the viscosity, density, and mixture properties of the fluent substance are factors to be considered. The rigidity and durometer of the valve material, and size and thickness of portions of both the valve head 160 and the intermediate portion 150 are additional factors to be considered.

The valve 56 in the first illustrated preferred embodiment of the flow control device 40 is intended in many applications to be opened axially outwardly when the pressure at within the housing inlet portion 44 exceeds the pressure within the housing outlet portion 48 by a predetermined amount. However, the valve head portion 160 can be deflected somewhat toward and against the platform 52 when the pressure on the outlet side 192 of the valve 56 exceeds the pressure on the valve inlet side 188 by a predetermined amount.

The opening of the valve 56 may be characterized as occurring in response to a predetermined opening pressure differential acting across the valve head portion 160. The valve 56 is designed to have a predetermined first, or minimum, opening pressure differential which causes the valve petals 212, 216 to initially begin to open to permit some flow of fluent substance through the valve 56. Preferably, this minimum opening pressure differential of the valve 56 is selected to be relatively small. In addition, the valve 56 is designed to open further to a pre-determined, desired ("design") cross-sectional flow area when the pressure differential across the valve head portion 160 is increased sufficiently to a greater, second opening pressure differential. Moreover, in some applications it is desired that the valve 56 be opened to its pre-determined, desired cross-sectional flow area at a second pressure differential that is less than a greater, specified pressure differential. That greater, specified pressure differential is known as the maximum, opening pressure differential. As used herein, the term "maximum opening pressure differential" is the specified pressure differential below which the valve 56 must reach its desired ("design") cross-sectional flow area to satisfy the flow requirements for the particular system in which the flow control device 40 will be used. In other words, the valve 56 must be opened to its pre-determined "design" cross-sectional flow area in response to a pressure differential that is greater than the minimum opening pressure differential but less than (and not equal to or exceeding) a greater specified pressure differential defined as the maximum opening pressure differential. In the illustrated preferred embodiment, the valve 56 will open to its pre-determined, desired cross-sectional flow area at some pressure differential that is greater than the minimum opening pressure differential and that also is less than a "maximum opening pressure differential" of about 15 mmHg. The selection of a desired predetermined minimum and maximum opening pressure differentials is determined in accordance with, inter alia, the flow criteria desired for a particular fluid substance, and/or the static head (if any), or other upstream or downstream pressure, that is exerted on the inlet side 188 or outlet side 192 of the valve 56.

When the valve 56 and the platform 52 are assembled or otherwise arranged within the housing 44, 48, 52, a space or interstitial region 220 is formed between the convex valve-confronting surface 120 of the platform 52 and the concave, inlet surface 188 of the valve head portion 160, the operation of which will be discussed in detail below.

In operation, the flow control device 40 functions in the following manner as is next described herein with reference to FIGS. 6 and 7. The pressurized fluent substance enters the housing inlet portion 44 through the inlet passage 66 and inlet orifice 68. The fluent substance fills the platform chamber 132 and flows through the plurality of apertures 134 (defined between the legs 124 of the platform 52) into the space or interstitial region 220 between the convex valve-confronting surface 120 of the platform 52 and the concave, inlet surface 188 of the valve head portion 160.

Initially, the valve 56 normally assumes an initial, normally closed configuration illustrated in FIGS. 6 and 7, wherein the valve 56 remains substantially in its original, as-molded shape without deformation (except perhaps at the flange 142 if the flange 142 is sufficiently compressively engaged by the housing inlet portion 44 and the housing outlet portion 48). When the valve 56 is in the normally closed configuration, the valve intermediate portion 150 is substantially unstressed, and the valve orifice slits 204, 208 are completely closed. In some applications (not illustrated), it may be desirable to configure the valve in relation to the platform such that there is some amount of tension or stress on the valve due to contact with the platform.

When a sufficient pressure differential is established across the valve head portion 160 (FIG. 7), such as when increased pressure is established on the valve inlet side 188 by entry of the fluent substance into the interstitial region 220 (or by an increase in pressure of fluent substance already present in the region 220), the valve petals 212, 216 open axially outwardly to create an open orifice in the manner illustrated in FIG. 8, and thereby dispense the fluid substance through the valve head portion 160. The fluent substance then enters the outlet chamber 104 and from there flows through the outlet orifice 98 and outlet passage 96, and out of the housing outlet portion 48 to a suitable tubing system (not illustrated) that is connected to the patient. The pressure differential causing the valve 56 to open may result solely from the upstream static head in the system, and/or from the operation of a manual or mechanical pumping action.

If the pressure at the valve outlet side 192 becomes greater than the pressure at the valve inlet side 188 owing to a reverse, or back, pressure differential established across the valve head portion 160 (such as during some abnormal or transient operation condition, for example by connecting or disconnecting an I.V. administration set or secondary administration set containing the flow control device 40 from a patient), then the reverse pressure differential may be great enough to cause the valve head portion 160 to be pressed axially inwardly toward the convex valve-confronting surface 120 of the platform 52. The shape and location of the platform 52 serve to prevent, or at least minimize, axially inward deflection (or even opening) of the petals 212, 216. The volume of the interstitial region 220 is also reduced by this axially inward movement of the valve head portion 160.

The inventors have found that providing a flow control device 40 with a platform 52, valve 56, and interstitial region 220 prevents, or at least minimizes, the potential for the valve 56 to become bridged or stuck on the open position. This is particularly true for fluent substances having suspended particulates, such as may be present in some intravenous medicaments. Some flow control devices of the prior art, especially prior art slit type disc valves, which do not have such an interstitial region adjacent the valve head inlet surface, may become stuck in at least a partially open position as suspended particles accumulate, in between ("bridge"), or around, the valve petals. Specifically, when some prior art valves are subjected to a back-flow pressure, the configuration or shape of localized portions of the prior art elastomeric valve petal or petals might undesirably be altered by the particulate such that the valve petal or petals might not fully close in a leak-tight manner. In contrast, the flow control device 40 of the present invention can accommodate some particulates without a significant adverse effect on the capability of the valve petals 212, 216 to close in a leak-tight manner.

The interstitial region 220 of the inventive flow control device 40 also minimizes the likelihood that the valve 56 would be undesirably engaged, and stressed by the platform 52 when assembled within the housing 44, 48, 52, as a result of manufacturing tolerances of the components of the flow control device 40.

Figure 13:
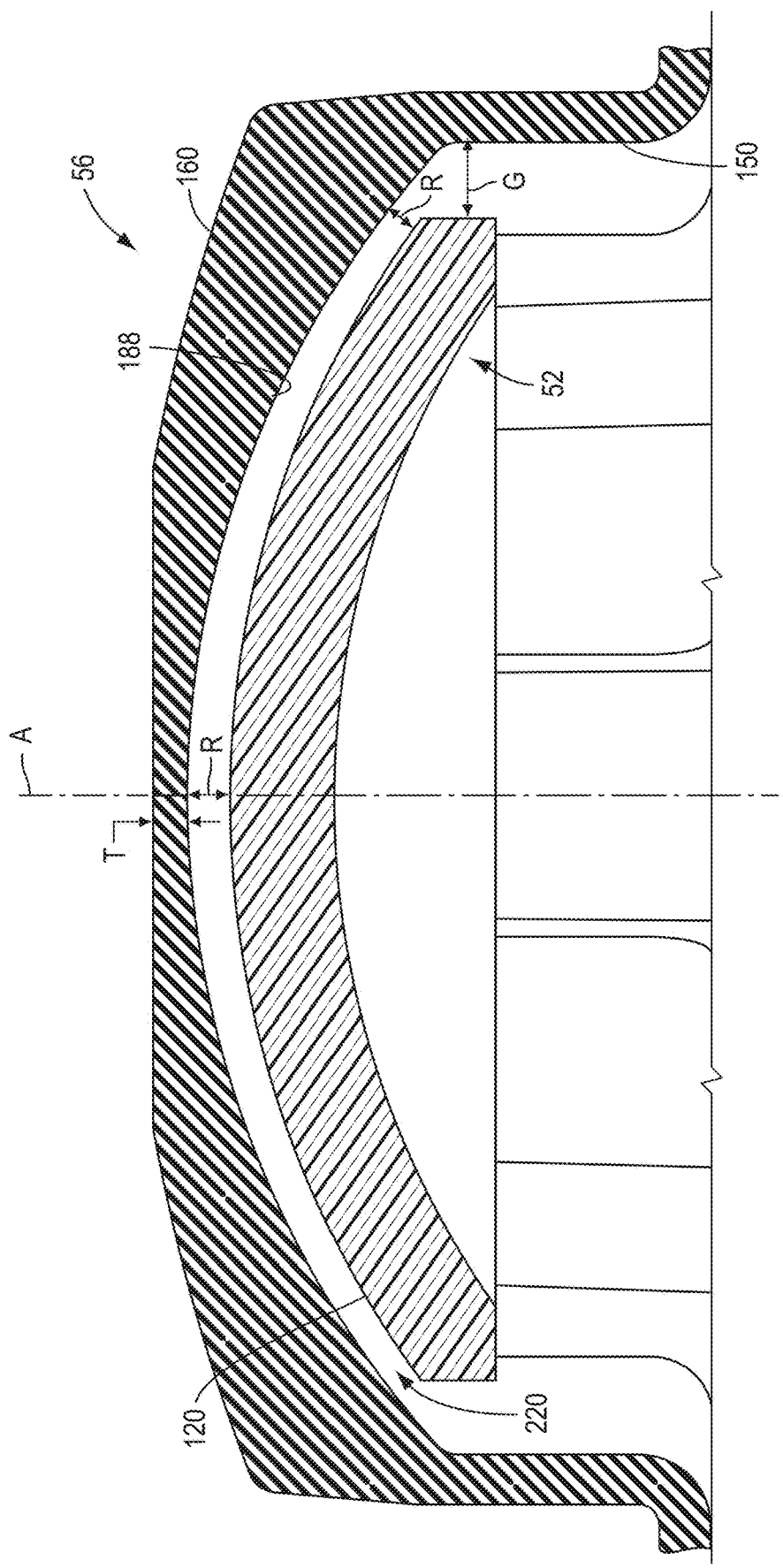
FIG. 13 is an enlarged, fragmentary, cross-sectional view of the central portion of the view shown in FIG. 6.

Referring to FIGS. 6, 7, and 13, the inventors have also found that providing a flow control device 40 with a platform 52 and valve 56 configured and arranged to define an interstitial region 220 maximizes the amount of surface area of the inlet surface 188 of the valve head portion 160 that is "exposed" to the fluent substance when the valve 56 is in the closed configuration. This feature is an improvement over some prior art flow control devices where the inlet surface of the valve head portion contacts an adjacent internal surface of the housing when the valve is in the closed configuration. Owing to the larger "exposed" inlet surface area of the present invention valve head portion 160 compared to some prior art configurations, the pressure differential required to open the valve 56 can be less than that of the prior art configurations. Specifically, compared to some prior art configurations, the present invention provision of the interstitial region 220 adjacent the inlet surface 188 of the valve head portion 160 allows the fluent substance to contact a larger area of the valve head portion valve inlet surface 188 and thereby establish a greater amount of torque to push and bend open the valve petals 212, 216, for a given pressure differential acting across the valve head portion 160. In contrast, in prior art configurations where the valve head portion inlet surface is in contact with an internal surface of the housing when the valve is in the closed position, the fluent substance cannot initially contact as much of the inlet surface of the of the valve head portion when the valve is closed. Compared to the present invention flow control device 40, such a prior art arrangement of the valve head portion inlet surface contacting an adjacent internal surface of the housing results in a lower initial torque on the valve petals for a given initial pressure differential.

The inventors have also found that the shape of the valve-confronting surface 120 and the volume between the valve-confronting surface 120 and the valve inlet side 188 can eliminate, or at least reduce, back flow of fluent material through the valve 56, from the outlet side 192 to the inlet side 188, when subjected to a back pressure to serve as a "check valve", as described above.

Furthermore, the inventors have found that a flow control device 40 with a valve 56 having an intermediate connecting portion 150, a portion of which is generally U-shaped, further reduces the likelihood of the valve 56 deflecting or opening axially inwardly when subjected to a back pressure (i.e., reverse pressure differential). It is additionally believed that the contact between the platform 52 and the U-shaped portion of the intermediate connection portion 150 of the valve 56 allows the flow control device 40 to withstand a greater back pressure.

Referring to FIG. 13, the inventors have found that, at least for some applications, it is particularly desirable to provide a flow control device 40 with a platform 52, a valve 56, and an interstitial region 220 arranged so as to achieve one or more of the following: (i) prevention, or at least minimization, of fluent substance backflow, and/or prevention or at least minimization, of some amount of the fluent substance remaining in the interstitial region 220 when the valve 56 moves from an open configuration to a closed configuration; (ii) provision of sufficient volume for containing a fluent substance upstream of, and adjacent, the valve head portion when the valve 56 is in the closed configuration so as to reduce the required opening pressure of the valve 56; and/or (iii) prevention, or at least minimization of, bridging of the petals of valve 56 in a way that would inhibit full closure of the valve 56. Preferably, the normal, or radial, distance R (FIG. 13) between a valve-confronting surface 120 of the platform 52 and an interior surface 188 of the valve 56 is between about 0.1 and about 0.5 mm, and more preferably is 0.2 mm. Preferably, the valve thickness T (FIG. 13) at the center of the valve 56 is also between about 0.1 and about 0.5 mm, and more preferably is about 0.2 mm. An annular gap G between the an intermediate connecting portion 150 of the valve 56 and the platform 52 is between about 0.2 and about 1 mm, and more preferably is about 0.5 mm.

It will be appreciated that while various theories and explanations have been set forth herein with respect to how the component configurations and arrangement may affect the operation of the valve 56 and the platform 52, there is no intention to be bound by such theories and explanations. Further it is intended that all structures falling within the scope of the appended claims are not to be otherwise excluded from the scope of the claims merely because the operation of such valve structures may not be accounted for by the explanations and theories presented herein.

Various modifications and alterations to this invention will become apparent to those skilled in the art without departing from the scope and spirit of this invention. Illustrative embodiments and examples are provided as examples only and are not intended to limit the scope of the present invention.

What is claimed is:

1. A flow control device for controlling the flow of a pressurized fluent substance, the flow control device comprising:
   A. a housing having
      1) an inlet portion defining an inlet passage for accommodating flow of a pressurized fluent substance,
      2) an outlet portion defining an outlet passage for accommodating flow of a pressurized fluent substance, and
      3) a platform;
   B. a valve located between said inlet passage and said outlet passage, said valve having
      1) a flexible, resilient head portion with
         a) an inlet surface facing said housing inlet passage,
         b) an outlet surface facing said housing outlet passage,
         c) at least one self-sealing slit through said head portion defining confronting, openable portions along said at least one self-sealing slit in an initially closed configuration, said openable portions being movable from said closed configuration to an open configuration when said head portion is subjected to an opening pressure differential acting across said head portion,
      2) a peripheral portion located laterally outward of said head portion for being retained by said housing, and
      3) an intermediate connecting portion extending between said head portion and said peripheral portion,
   wherein said platform is
      1) located between said valve inlet surface and said housing inlet passage, and
      2) configured to be abutted by said valve inlet surface when the pressure at said valve outlet surface exceeds the pressure at said valve inlet surface by a predetermined amount; and
   wherein said valve intermediate connecting portion contacts said platform and said housing inlet portion when said valve openable portions are in said initially closed configuration,
   wherein said platform is a component that is separately molded from, but attached to, said housing inlet portion, and 1) said platform has at least one leg, and
2) said inlet portion has at least one retaining bead for engaging said at least one leg.

2. The flow control device in accordance with claim 1 wherein said platform is spaced a predetermined distance from said valve inlet surface when said valve openable portions are in said initially closed configuration.

3. The flow control device in accordance with claim 2 wherein said platform is spaced from said valve inlet surface a normal distance between about 0.1 and 0.5 mm.

4. The flow control device in accordance with claim 3 wherein said platform is spaced from said valve inlet surface a normal distance of about 0.2 mm.

5. The flow control device in accordance with claim 1 wherein said platform further comprises
1) an arcuate valve-confronting surface for abutting said valve, and
2) at least one aperture for accommodating flow of a pressurized fluent substance.

6. The flow control device in accordance with claim 5 wherein said platform comprises a plurality of apertures located axially inwardly of said arcuate valve-confronting surface.

7. The flow control device in accordance with claim 1 wherein said valve inlet surface is generally concave and said valve outlet surface is generally convex, and a central portion said outlet surface is flat.

8. The flow control device in accordance with claim 1 wherein
1) said housing outlet portion has a frustoconical seating surface; and
2) one of said housing inlet portion and said platform has an annular channel for receiving said peripheral portion of said valve.

9. The flow control device in accordance with claim 1 wherein said valve head portion is substantially thicker than said valve intermediate connecting portion at the location where said valve intermediate connecting portion connects to said valve head portion.

10. The flow control device in accordance with claim 1 wherein said valve head portion and said platform are configured so that
1) when the pressure at said valve outlet surface exceeds the pressure at the valve inlet surface by a predetermined amount,
2) then said platform contacts a major portion of said valve inlet surface.

11. The flow control device in accordance with claim 1 wherein at least part of said intermediate connecting portion defines a generally U-shaped configuration as viewed along a longitudinal cross-section through said valve when said openable portions are in said initially closed configuration.

12. The flow control device in accordance with claim 1 wherein said at least one self-sealing slit comprises a pair of major intersecting slits, and each of said major intersecting slits terminates in a pair of diverging minor slits.

* * * * *